(12) United States Patent
Schumacher et al.

(10) Patent No.: US 10,881,297 B2
(45) Date of Patent: Jan. 5, 2021

(54) IN-SITU SENSOR

(71) Applicants: TECHNISCHE UNIVERSITAT HAMBURG, Hamburg (DE);
UNIVERSITATSKLINIKUM HAMBRUG-EPPENDORF (UKE), Hamburg (DE)

(72) Inventors: Udo Schumacher, Hamburg (DE);
Wolfgang Krautschneider, Hamburg (DE); Dietmar Schroder, Uelzen (DE)

(73) Assignees: TECHNISCHE UNIVERSITÄT HAMBURG, Hamburg (DE);
UNIVERSITÄTSKLINIKUM HAMBRUG-EPPENDORF (UKE), Hamburg (DE)

( * ) Notice: Subject to any disclaimer, the term of this patent is extended or adjusted under 35 U.S.C. 154(b) by 120 days.

(21) Appl. No.: 16/310,034

(22) PCT Filed: Jun. 16, 2017

(86) PCT No.: PCT/EP2017/064758
§ 371 (c)(1),
(2) Date: Dec. 14, 2018

(87) PCT Pub. No.: WO2017/216333
PCT Pub. Date: Dec. 21, 2017

(65) Prior Publication Data
US 2019/0328230 A1    Oct. 31, 2019

(30) Foreign Application Priority Data
Jun. 16, 2016   (LU) .......................................... 93109

(51) Int. Cl.
*A61B 5/00* (2006.01)
*A61B 5/03* (2006.01)
(Continued)

(52) U.S. Cl.
CPC .......... *A61B 5/0031* (2013.01); *A61B 5/0015* (2013.01); *A61B 5/036* (2013.01);
(Continued)

(58) Field of Classification Search
CPC ............ A61B 5/0002–0031; A61B 2560/0209
See application file for complete search history.

(56) References Cited

U.S. PATENT DOCUMENTS

2008/0161713 A1* 7/2008 Leyde .................. A61B 5/0006
600/544
2008/0306359 A1   12/2008 Zdeblick et al.
(Continued)

FOREIGN PATENT DOCUMENTS

WO    WO 2016/044651    3/2016

OTHER PUBLICATIONS

John et al. "Wireless Blood Pressure Measurement Implant Electronics for Integration in a Stent Graft," Biomedical Engineering, Feb. 2016, pp. 155-159.
(Continued)

*Primary Examiner* — Lynsey C Eiseman
(74) *Attorney, Agent, or Firm* — Sheridan Ross P.C.

(57) ABSTRACT

The invention proposes an In-situ Sensor (1) for being implanted within tissue of a mammal (P) comprising •an energy harvesting portion (RX), •a communication portion (TX), •a pressure sensor ($S_P$) for measuring interstitial pressure of surrounding tissue when located within tissue, •a further sensor ($S_F$), whereby the further sensor is selected from a group comprising pH sensor, lactate sensor, impedance sensor, radiation sensor, temperature sensor, sensor for bioelectrical potentials, •whereby said further sensor ($S_F$), said pressure sensor ($S_P$) as well as the communication portion (TX) are powered by the energy harvesting portion (RX), •whereby information indicative of the measurement
(Continued)

Figure 1:
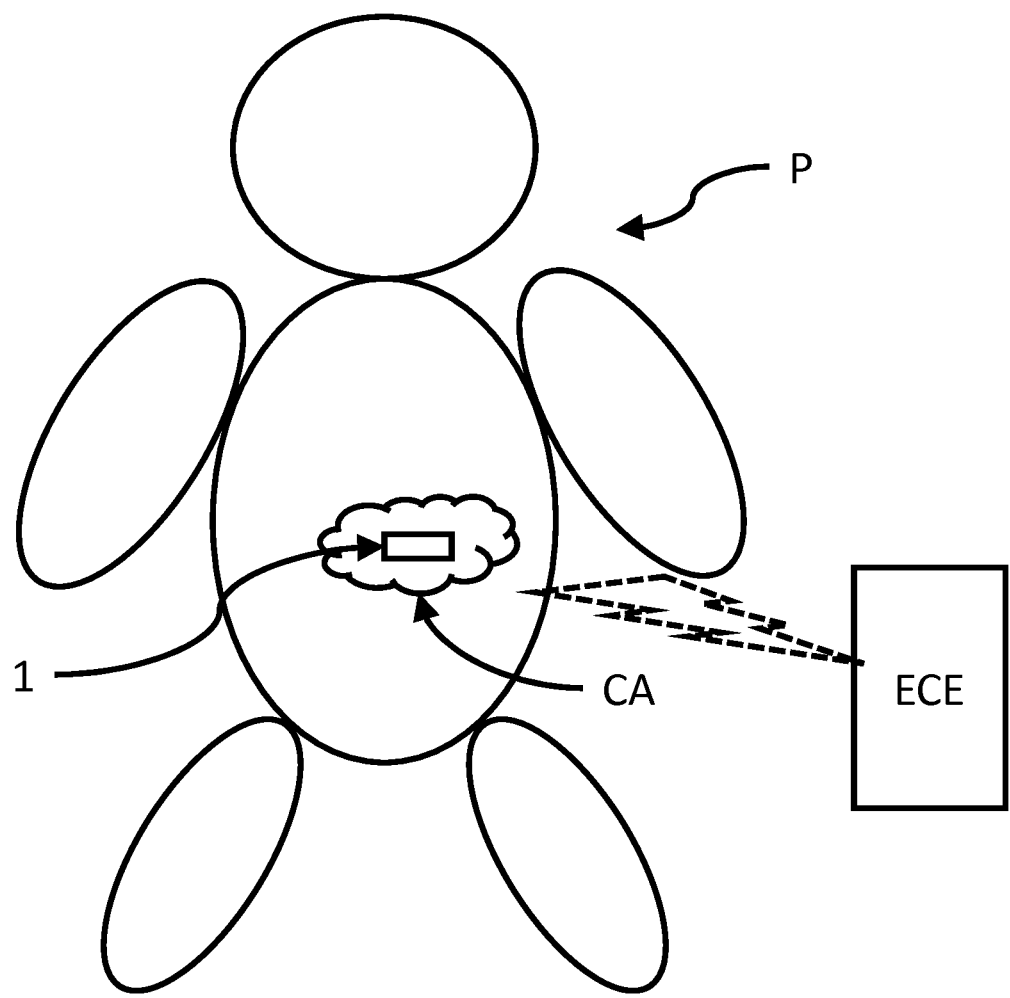

provided by the pressure sensor ($S_P$) and data indicative of the measurement provided by said further sensor ($S_F$) is communicated via said communication portion (TX) towards an extracorporeal receiving entity (ECE), •whereby said communication portion (TX) and/or said pressure sensor ($S_P$) and/or said further sensor ($S_F$) are adaptable such that they consume less energy in case storage of energy by the energy harvesting portion (RX) drops below a certain threshold.

17 Claims, 3 Drawing Sheets

(51) Int. Cl.
*H03M 1/12* (2006.01)
*H04B 1/02* (2006.01)

(52) U.S. Cl.
CPC ............... *A61B 5/686* (2013.01); *H03M 1/12* (2013.01); *H04B 1/02* (2013.01); *A61B 2560/0219* (2013.01); *A61B 2562/0247* (2013.01); *A61B 2562/0271* (2013.01); *A61B 2562/17* (2017.08)

(56) References Cited

U.S. PATENT DOCUMENTS

| | | | |
|---|---|---|---|
| 2013/0345525 A1 | 12/2013 | Kline | |
| 2017/0325710 A1* | 11/2017 | Ryan | G01R 33/288 |
| 2018/0125365 A1* | 5/2018 | Hunter | A61B 5/6812 |

OTHER PUBLICATIONS

Ponce et al. "Trade-off Study on Switched Capacitor Regulators for Implantable Medical Devices," ICT.OPEN2017, Mar. 2017, pp. 4-7.
Ranjan et al. "Capacitance to Digital Converter ASIC with Wireless Energy and Wireless Data Transmission for a Medical Implant," ITG-FACHBERICHT 266: Analog 2016, Sep. 2016, pp. 93-97.
Official Action for Luxembourg Patent Application No. 93109, dated May 16, 2017, 10 pages.
International Search Report and Written Opinion prepared by the European Patent Office dated Sep. 6, 2017, for International Application No. PCT/EP2017/064758.

* cited by examiner

IN-SITU SENSOR

CROSS REFERENCE TO RELATED APPLICATIONS

This application is a national stage application under 35 U.S.C. 371 and claims the benefit of PCT Application No. PCT/EP2017/064758 having an international filing date of 16 Jun. 2017, which designated the United States, which PCT application claimed the benefit of Luxembourg Patent Application No. 93109 filed 16 Jun. 2016, the disclosure of each of which are incorporated herein by reference.

BACKGROUND

Within the medical field numerous therapies are available. However, some of these therapies are not easy to track with respect to their long-term effect and/or their efficacy. In the following we will describe such conditions with respect to benign or malign tissue. However, the invention is not limited thereto.

Treatment of malign tissue—more often referred to as cancer treatment—often involves some sort of radiation therapy and/or chemo therapy. Some of these therapies may be focused towards the target area while others are less selective.

These therapies in addition to their intended effect do also encompass side-effects, e.g. they also impair surrounding tissue as well as distant cells.

However, efficacy thereof is to some extent unpredictable. When trying to define a dosage regime, it is often a trade-off between minimizing side-effects while still providing a desired effect.

Even when a cancerous tissue has been successfully treated, there is still an increased probability that one or more cancerous cell survived which may lead to a relapse.

In addition some cancerous tissue growth, such as prostate cancer, is kept under active surveillance as the impact of surgery and/or therapy is sometimes held inappropriate in comparison to an expected life time of a patient.

In order to minimize the risks of a relapse and or to detect a sudden (re-)growth, a close surveillance of the therapy as well as after completion of therapy is necessary. However, such surveillance is often expensive and time-consuming. In addition detecting of some of this tissue (and its growth/shrinkage to due therapy) is rather complicated as some of the tissue growth may not be visualized by today's imaging technologies. I.e. the efficacy of a therapy may only be determined after valuable time has been lapsed before imaging technologies allow for a reliable diagnosis with respect to therapy efficacy.

Knowing this background, it would be helpful to find a measure allowing for detecting efficacy of a treatment on a short term basis as well as on a long term basis.

SHORT DESCRIPTION OF THE INVENTION

To overcome one or more problems in the art, the invention proposes an in-situ sensor which is able to monitor various effects occurring during treatment.

The in-situ Sensor for being implanted within tissue of a mammal an energy harvesting portion, a communication portion, a pressure sensor for measuring interstitial pressure of surrounding tissue when located within tissue, a further sensor, whereby the further sensor is selected from a group comprising sensor such as pH sensor, lactate sensor, impedance sensor, radiation sensor, temperature sensor, sensor for bioelectrical potentials, whereby said further sensor, said pressure sensor as well as the communication portion are powered by the energy harvesting portion, whereby information indicative of the measurement provided by the pressure sensor and data indicative of the measurement provided by said further sensor is communicated via said communication portion towards an extracorporeal receiving entity, whereby said communication portion and/or said pressure sensor and/or said further sensor are adaptable such that they consume less energy in case storage of energy by the energy harvesting portion drops below a certain threshold.

Further details are subject to the dependent claims and the description.

SHORT SUMMARY OF THE FIGURES

Figure 2:
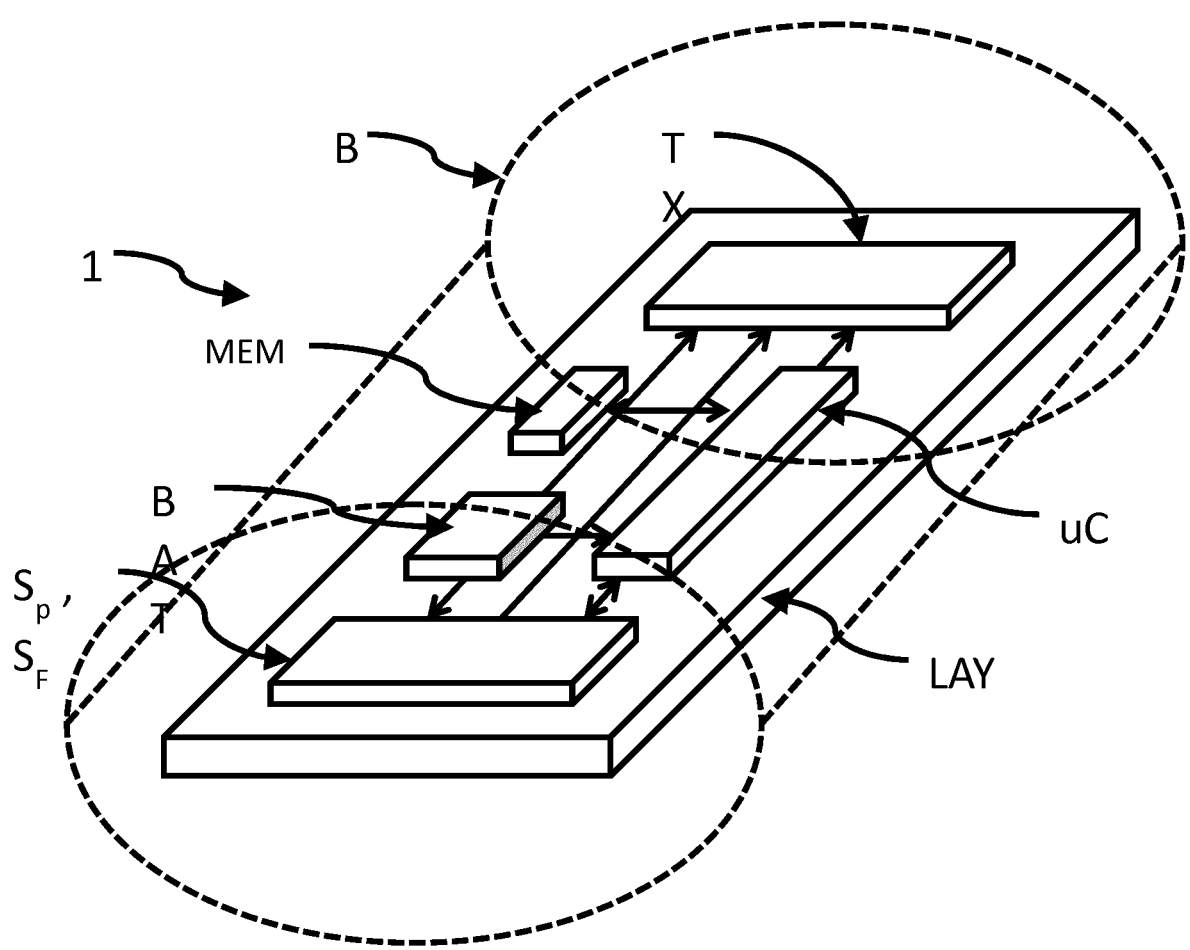
Figure 3:
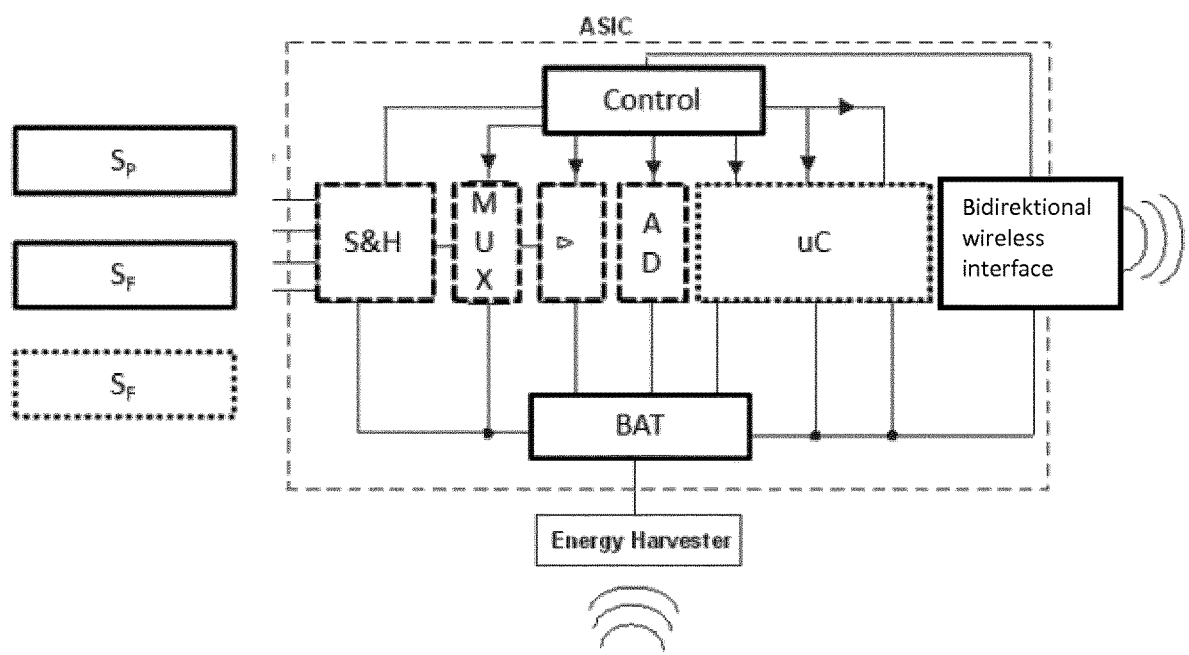

In the following detailed description reference will be made towards the figures, in which FIG. 1 shows a schematic overview of an in-situ sensor and an extracorporeal receiving entity according to the invention, FIG. 2 shows a schematic overview of the an in-situ sensor according to FIG. 1, and FIG. 3 shows a schematic electronic arrangement of components of the in-situ sensor according to FIG. 1.

DETAILED DESCRIPTION

The present disclosure describes preferred embodiments with reference to the Figures, in which like reference signs represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, method steps or characteristics of the invention may be combined in any suitable manner in one or more embodiments. In the description, numerous specific details are recited to provide a thorough understanding of embodiments of the invention.

I.e., unless indicated as alternative only any feature of an embodiment may also be utilized in another embodiment.

In addition, even though at some occurrences certain features will be described with reference to a single entity, such a description is for illustrative purpose only and actual implantations of the invention may also comprise one or more of these entities. I.e. usage of singular also encompasses plural entities unless indicated.

The invention proposes an in-situ Sensor 1 for being implanted within tissue of a mammal P, see FIG. 1.

The in-situ sensor 1 comprises an energy harvesting portion RX, a communication portion TX.

The in-situ sensor 1 comprises also a pressure sensor $S_P$ for measuring interstitial pressure of surrounding tissue when located within tissue, and at least a further sensor $S_F$.

The further sensor $S_F$ is selected from a group comprising sensors such as pH sensor, lactate sensor, impedance sensor, radiation sensor, temperature sensor, sensor for bioelectrical potentials.

The sensors, i.e. the further sensor $S_F$ and said pressure sensor $S_P$, as well as the communication portion TX are powered by the energy harvesting portion RX.

Information indicative of the measurement provided by the pressure sensor $S_P$ and data indicative of the measurement provided by said further sensor $S_F$ is communicated via said communication portion TX towards an extracorporeal receiving entity ECE.

The invention thereby takes benefit that within cancerous tissue the local pressure within the tissue is increased in comparison to normal tissue. One effect contributing thereto is decreased lymph drainage.

To allow the sensor to operate autonomous for an extended period, the communication portion TX and/or the pressure sensor $S_P$ and/or the further sensor $S_F$ are adaptable such that they consume less energy in case storage of energy by the energy harvesting portion RX drops below a certain threshold.

In the following we will describe the concept. The in-situ sensor 1 comprises the energy harvesting portion RX, which may comprise a reservoir for locally storing energy such as a capacitor. To allow for providing energy for an extended period, an energy management system may be employed allowing for adjusting the energy consumption of components of the in-situ sensor 1 in accordance with a stored energy by the energy harvesting portion RX.

In embodiments of the invention said pressure sensor $S_P$ and/or said further sensor $S_F$ comprise an amplifier PA and an Analog-to-Digital Converter ADC.

The power consumption of a sensor, the pressure sensor $S_P$ and/or the further sensor $S_F$, is mainly determined by the amplifier and the analog-to-digital converter.

The power consumption of the amplifier can be controlled by a bias current. But, less power consumption results in greater noise of the amplifier, i.e. the signal-to-noise ratio is worsened.

Less resolution of the analog-to-digital converter reduces the required power in an exponential manner, and reduces the signal-to-noise ratio as well.

I.e., by an appropriate choice of the resolution of the analog-to-digital converter (ADC) and the noise floor of the amplifier, a trade-off between signal quality and current consumption allows for increased operation times compared to a fixed resolution respectively a fixed noise floor.

A high signal-to-noise ratio may be achieved by either making the signal amplitude high, or the noise low, or both. Strong signal is achieved e.g. by operating the sensor with a high bias voltage or current, or by making the amplification factor of the first stage of the sensor interface large, which requires a high output swing, which in turn is achieved by a high bias current of the output stage. The overall noise of the system is dominated by the noise of the first stage; low noise is therefore achieved if the noise of the input transistors is made small. The input-referred thermal noise of the input transistors is inversely proportional to the bias current of the transistors. Hence, low thermal noise of transistors must be paid for by a high bias current and thus high energy consumption.

Sensor readings with high precision are digitally represented by a large number of bits (high resolution). Transmitting the readings wirelessly to an external reader device therefore requires the transmission of many bits in a given timeframe. As the communication module is characterized by a certain amount of energy consumption per transmitted bit, this requirement results in large energy consumption of the communication module.

The sensors $S_P$ and/or $S_F$ may therefore be constructed in such a way that the signal-to-noise ratio can be selected, e.g. by a control unit. Similarly, the analog-digital converter ADC may be constructed in such a way that its resolution can be selected, e.g. by a control unit.

Because the signal-to-noise ratio of the sensors $S_P$ and/or $S_F$ is dependent on the bias currents or voltages (operation point) of a respective transducer and a respective first stage of the sensor interface, the signal-to-noise ratio can be externally controlled via these parameters. Therefore, if the operation point may be set by current or voltage source circuits whose values can be digitally selected, it is possible to control the signal-to-noise ratio of the sensors $S_P$ and/or $S_F$, e.g. by a digital control unit.

In a successive-approximation analog/digital converter (SA-ADC), the output bits are generated successively by i) providing a comparison threshold using a digital-to-analog converter (DAC) and ii) by comparing this threshold with the input value in each step using a comparator. If the digital control circuit of the SA-ADC is constructed in such a way that it can be stopped after a selectable number of steps, the resolution of the SA-ADC and therefore the number of bits per sample can be externally selected.

An improved flexibility is achieved if the resolution can be set to any integer number between 1 and the maximum resolution. In the extreme case of a resolution of 1, the operation of the ADC reduces to a simple threshold comparison.

If the resolution of the ADC is reduced, some parts of the DAC are not used and can be switched off, thereby saving energy consumption. Because the parts of a DAC that are related to the most-significant-bits (MSBs) consume most of the energy, it is preferred to switch off the MSB parts of the DAC hardware in a reduced resolution situation rather than the LSB parts, although from the point of view of digital representation of sensor values, it is the LSBs that are excluded in this situation.

The in-situ sensor 1 may automatically monitor the available amount of power or energy stored within the energy harvesting portion RX. If the energy resources fall below some predefined threshold, the in-situ sensor 1 may automatically reduce energy consumption in such a way that the said pressure sensor $S_P$ and/or said further sensor $S_F$ operate with a lower signal-to-noise ratio, and/or the analog-digital converter operate with a lower resolution, which results in a lower number of bits to be transmitted and thus a smaller data rate of the communication portion TX.

Logical blocks of the energy harvesting portion (RX) may comprise:
- an inductor or a coil (energy harvester) for collecting inductively coupled energy
- a CMOS rectifier, e.g. in high-voltage technology, for rectifying with high efficiency. The rectifier provides the input voltage Vin for the charge pump
- a first charge pump with the output voltage Vout and a variable pumping ratio Vout/Vin. Vout is regulated in a way that it is greater than the voltage at the energy reservoir Vres.
- an energy reservoir that can be charged up very fast. This energy reservoir can be realized, e.g., by a capacitor. As the energy stored in a capacitor is proportional to the square of its voltage, the first charge pump will provide an output voltage Vout as high as possible for storing as much energy as possible.
- voltage Vres may be adapted (reduced or increased) by a second charge pump in order to provide the supply regulator with a voltage (just) above the supply voltage Vdd of the electronic circuits.

a capacitor at the input of the supply regulator provides the additional energy for short current peaks of the electronic circuits.

a supply regulator provides a constant voltage Vdd at its output to power the electronic circuits.

In the proposed energy harvesting architecture, a second charge pump may transfer energy from a storage capacitor to the input capacitor of the supply regulator. For this purpose, the charge pump circuitry may evaluate the voltages on both capacitors in order to transfer energy just as needed; and avoid energy to be transferred unnecessarily during the transfer.

A digital representation of the energy available stored within such a storage capacitor of the energy harvesting portion RX may be generated by a tiny evaluation circuit. The digital representation may be used by (e.g. a control unit) to adapt the signal-to-noise ratio of the interfaces of the pressure sensor $S_P$ and/or the further sensor $S_F$ and the resolution of the ADC to the available amount of energy indicated by the digital representation.

The invention benefits also from the finding that pressure and temperature values to be measured by the In-situ Sensor 1 are changing rather slowly over time.

Therefore, it is possible (e.g. by a control unit) to estimate the values to be measured at the next sampling instant with relatively low computational effort. (In the most simple embodiment, it simply uses the value measured at the previous sampling instant as the prediction for the next instant, in which case no computational effort is needed at all.)

The analog-digital converter ADC may also be constructed in such a way that it uses the estimated value for narrowing down the amplitude region in which the measured value is to be searched. Thereby, it can determine the digital code for the measured value with less number of operations, i.e. less generation of threshold values by a digital-analog converter or less comparisons with the threshold by a comparator circuit. The reduction of the number of operations results in a lower energy consumption of such analog-digital converter.

The output of the analog-digital converter ADC may then contain fewer number of bits compared to the binary search as in conventional analog-digital converters. In other words, the analog-digital converter automatically may generate a compressed version of the digital sensor value representation. If a smaller number of bits are to be stored and/or transmitted, energy consumption may be reduced accordingly.

The ADC may be constructed in such a way that it automatically generates a compressed encoding (such as Huffman encoding) of the input value. The code may be defined by a corresponding code tree, which is predefined on both the encoder and decoder side. The code tree may be constructed in such a way that the length of the code for a particular sample value is small for frequently occurring values and may be large for rarely occurring values, thereby ensuring that on average the information is transferred with the minimum number of bits. The lengths of the codes may be inherent in the code itself, such that extra bits for transmitting the code length of a sample are not necessary.

For self-testing of the electronic circuits a test pattern generator provides test signals with different amplitudes, e.g. a small, middle-sized or large amplitude. These amplitudes may be fed into the system that is operated using (e.g. three) different energy modes, e.g.

i) high energy in the storage capacitor,
ii) medium energy and
iii) low energy.

The digital output signals may be compared with stored signals. If the signals are consistent, a "pass" is stored, if not, a message is sent to the reader device.

The electronic circuitry may be twofold placed on a supporting Layer LAY. The same procedure may be performed with the second circuitry. When both the circuits achieve "pass", the functionality of the chip is assured.

The grading of the amplitudes of the test pattern generator can be made smaller or larger depending on the specifications of the test procedure.

The implant may monitor the available amount of power or energy. If the energy resources fall below some prescribed threshold, the In-situ Sensor 1 may adapt, i.e. reduce, the energy consumption by decreasing the sampling rate.

The digital circuits on the In-situ Sensor 1 or parts thereof (e.g. a control circuit of the ADC) may be implemented in adiabatic logic or quasi-adiabatic logic, thereby reducing the energy consumption of the In-situ Sensor 1 in comparison to using conventional logic. Adiabatic logic is more efficient when operating at slower speeds; therefore, because the sampling rate of the system is rather low, high speed is not necessary, and adiabatic logic may be a viable option.

In adiabatic or quasi-adiabatic logic, the power supply of the stages of a logical function, consisting of logic gates, is slowly ramped up or down, thereby reducing the energy dissipation in the logic gates. In order to function properly, the stages must be ramped up or down successively, i.e. a stage must be ramped up or down not before the previous stage has completed its logic operation.

If the digital circuits are implemented in adiabatic logic, lower sampling rate results in lower operating speed, which in turn results in lower energy consumption by nature of adiabatic logic.

The inductors present on the In-situ Sensor 1 may be synergistically used to generate the clock-like power supply for adiabatic logic. Thereby, putting extra inductors for this purpose on the implant is not necessary.

In quasi-adiabatic logic, the charging of some capacitor to a given voltage may be carried out by plural paces of lower voltage steps, thereby reducing the energy consumption of the process. In the presence of a step-up DC/DC converter (charge pump) in the energy harvesting unit RX of the In-situ Sensor 1, these intermediate voltage levels may be existing anyway inside the DC/DC converter and may be used for the quasi-adiabatic charging. Thereby, extra generation of the intermediate voltage levels is not necessary.

It is known, that the local pressure fluctuates over a day. It is also known that local pressure impedes a transfer of pharmaceutical agents such as a cytostatic drug into cancerous tissue CA.

Hence, knowledge of local pressure (sometimes referred to as interstitial [fluid] pressure) and/or its typical variation over time allows for a precise timing such that pharmaceutical agents may be administered within a favorable period of lower local pressure.

Such a favorable period may also be detected when taking into account the results of a further (different) sensor. This is particular valuable as the local pressure may not always be (alone) indicative for a cancerous growth. I.e. while a certain cancer type may allow for determination due to an increase in pressure another one might not.

That is, an increased temperature as well as other parameters such as acidity (pH), electrical impedance, etc. may be used to determine metabolic reactions and/or reactions caused by interaction with a therapeutic agent and/or radiation within the respective tissue. I.e. a change of one or more parameters may be used as indication of an increase of cancerous tissue indicating that a therapy needs to be altered/resumed or a decrease of cancerous tissue indicating that a therapy is effective.

Hence, the invention allows not only for tracking a therapy on-line, it also allows for long-term surveillance without the need for expensive technology. Hence, in case a therapy does not provide for the desired effect a change in therapy may be advised earlier than in prior art. Also, due to the direct determination a more precise dosage regime may be enacted.

In case the in-situ sensor is to be used in connection with radiation therapy, the in situ sensor 1 allows for such uses as well. Due to an electronic design allowing for strong differential signals the in-situ design is robust versus radiation impact. Such a design may be based on mixed mode circuits comprising e.g. thick oxide MOS transistors to be operated at greater voltages. Hence, the effect of parasitic charges due to radiation may be kept low.

Even the effect of degradation due to radiation may be compensated and/or measured for compensation. Although not expressly mentioned yet, a further sensor $S_F$ may also allow for detecting radiation and/or degradation, whereby radiation may be locally administered radiation such as when using brachy-therapy as well as extracorporeal and/or inter-operative radiation therapy. Such a further sensor $S_F$ may be monitored e.g. via bandgap reference voltage sources allowing to generate a precise current. Since the generated current is insensitive versus radiation it may be used as a reference. E.g. when the generated current is applied towards a (MOS-) transistor acting as impedance, the voltage drop at the impedance may be measured. In case of parasitic charges due to radiation impact the voltage drop is varying. Hence a variation of the voltage drop allows for determining radiation impact.

According to an embodiment of the invention the energy harvesting portion RX is arranged to harvest energy provided by external electromagnetic fields.

E.g. by usage of a certain alternating electro-magnetic field, energy as well as data may be transferred from an extracorporeal "receiving" entity ECE as well as the extracorporeal "receiving" entity ECE may actually receive (as well as retrieve) data from one or more in-situ sensor 1 within range. Also communication parameters may be negotiated to ensure reliable communication while consuming low energy.

It is to be noted that although the communication portion TX as well as the energy harvesting portion RX may be embodied in a single entity.

Hence, data exchange is not limited to a unidirectional transport but the in-situ sensor 1 may be inquired with respect to data but may as well be controlled/programmed to perform measurements/calculations/drug dispensing according to a prescribed scheme.

If a number of in situ-sensors are placed at different positions within a cancerous tissue CA, local effects may be observed when retrieving data. Hence, retrieving local data (as well as a time stamp) of a respective in-situ sensor 1 and correlating the data to its location and other data of the therapy such as a radiation profile may allow for a precise management of a therapy. In order to distinguish in-situ sensors one another it may be foreseen that each in-situ sensor 1 respectively each sensor thereof may be identifiable by a unique identification ID which is sent along when delivering data towards an extracorporeal receiving entity ECE.

In an embodiment of the invention the communication portion TX (or an additional evaluation entity uC) is arranged to evaluate sensor data received from the pressure sensor $S_P$ and/or said further sensor $S_F$ before communicating information indicative of the respective measurement. Such a pre-processing may allow reducing the energy consumption as pre-processing may consume less energy than transmission of raw data sets. In addition, some data may already be present at an extracorporeal receiving entity ECE and as such there is no need to transport this data twice. Evaluation may comprise comparison of measured data versus one or more (pre-) set threshold(s) and/or combinations of data originating from the pressure sensor $S_P$ as well the further sensor $S_F$. Evaluation may be customized towards a specific cancer type as well as customized with respect to a certain therapy or even an individual patient. Evaluation may be performed hard-coded, i.e. by a certain circuitry, and/or soft-coded, i.e. within software.

In an embodiment of the invention, the in-situ sensor 1 also comprises a storage portion MEM for storing information indicative of the respective measurements. Hence, there is no need for having a sensor transmitting data on-line. Such a memory MEM may allow accumulating data such that transmission thereof is most effective. I.e. when using a packetized protocol it is preferable to accumulate enough data such that a complete data package may be filled so that no empty bits are transferred.

In an embodiment of the invention the communication portion TX is conforming to a Near Field Communication Standard. Near field communication standard may be NFC, ZigBee, Bluetooth, Bluetooth Low Energy, RFID, and the like.

Although no specific type of pressure sensor $S_P$ has been described so far, in a preferred embodiment the pressure sensor $S_P$ is based on, e. g., piezo-effect or capacitance variation. Such an approach allows for high signal amplitudes thereby providing reliable signals even when being used while radiation may be applied.

According to an embodiment some components as well as the in-situ Sensor 1 as a whole—see FIG. 2—(but the sensing areas) may comprise a body B comprising a biocompatible covering COV whereby said energy harvesting portion RX and said communication portion TX are arranged within the body B. Such an approach allows for easy delivery, e.g. via biopsy needle, as well as reducing (unwanted) interaction of the surface with tissue of a mammal P.

In a preferred arrangement the biocompatible covering COV comprises PTFE.

According to an embodiment of the in-situ sensor 1 is formed for delivery into tissue CA of a mammal P by means of a biopsy needle having a size of Gauge G10 or smaller size.

In doing so, a sensor may be applied when taking a punch biopsy. I.e. the impact is minimized and a further (traumatic) intervention is avoided. Such a placement of an in-situ sensor 1 may even be performed as outpatient treatment. In order to allow delivery via a biopsy needle the in-situ sensor 1 allows for using technologies such as Application Specific Integrated Circuits (ASICs)—see e.g. FIG. 3—as well as System-on-Chip (S-o-C) arrangements. These approaches of high integration allow consolidating numerous functions within a reduced number of components. In particular an energy harvesting portion RX, a communication portion TX may be integrated as well as amplification elements L. and A/D-converters and Multiplexers MUX and Sample&Hold circuitry S&H for sensor signals. In addition an evaluation unit uC may be integrated allowing for data processing and compression. Furthermore, energy storage is displayed in a generalized manner as BAT. Energy storage may be composed of a (high capacity) capacitor.

In embodiments of the invention said pressure sensor $S_P$ and/or said further sensor $S_F$ comprise an amplifier PA and an Analog-to-Digital Converter ADC. The amplifier PA may—at the expense of lower Signal-to-Noise Ratio—be driven at a lower current when storage of energy by the energy harvesting portion RX drops below a certain threshold.

That is, by adapting the power consumption the in-situ sensor may be used for a prolonged time.

In embodiments of the invention said pressure sensor $S_P$ and/or said further sensor $S_F$ comprise an amplifier PA and an Analog-to-Digital Converter ADC, whereby said Analog-to-Digital Converter ADC—at the expense of Resolution—is adjusted to a lower resolution when storage of energy by the energy harvesting portion RX drops below a certain threshold.

That is, by adapting the power consumption the in-situ sensor may be used for a prolonged time.

In embodiments of the invention said pressure sensor $S_P$ and/or said further sensor $S_F$ comprise an amplifier PA and an Analog-to-Digital Converter ADC, whereby said Analog-to-Digital Converter ADC is arranged to adapt the measurement based on a previous measurement.

That is, by adapting the measurement less energy is consumed allowing for the in-situ sensor to be used for a prolonged time.

In embodiments said Analog-to-Digital Converter ADC adapts the measurement such that a compressed encoding of the information (e.g. a Huffman encoding) indicative of the measurement is generated.

It is to be noted that the radiation sensor (as a sample further sensor) as described may be a radiation damage sensor.

In embodiments of the invention at least some of the portions of the In-Situ Sensor 1 are implemented in adiabatic or quasi-adiabatic logic.

As described the In-situ Sensor 1 according to the invention may particularly be used within a malign or benign tissue.

Even though not described in detail, the in-situ sensor may as well allow for acting as an in-situ actor. E.g., the in-situ sensor 1 may be active in that electrodes on the surface of the body B are activated such to generate (alternating or steady) electrical fields. It has been described that electrical fields may inhibit growth of cancerous cells. In particular, electrical field may influence concentration of ions as well as velocity and direction of ions within cells. Hence, applying electrical fields influences ions within cells and thereby impacts cell division and vitality of cells in general. By applying alternating electrical fields cells within cancerous tissue CA are disabled. The effect of disablement may be determined by the in-situ sensor 1 via its sensors. Hence, the measurements may be feed back to control parameters of the alternating electrical field such as frequency, amplitude, waveform.

It may also alternatively or in addition be foreseen that the in-situ sensor 1 dispenses certain therapeutic agents. In that case a reservoir and dispensing system may be foreseen.

The application of electrical fields and/or dispensing of drugs may be controlled remotely, e.g. via the extracorporeal "receiving" entity ECE as well as locally, e.g. the in-situ sensor 1 dispenses according to a prescribed time scheme and/or in response to certain data measured by the in-situ sensor 1 a certain amount of one or more drug(s). Hence, a therapy may be more precisely controlled leading to superior results in therapy.

In addition, due to the direct response, it is possible to test a number of drugs by one or more in-situ sensors 1 located within a cancerous tissue CA in that a direct response thereto is determined allowing to detect a most efficient drug with respect to a certain cancer. Hence, the knowledge of a most effective drug within a small region may be used as a decisive criterion when selecting a global therapy.

The invention claimed is:

1. An in-situ sensor for being implanted within tissue of a mammal, the in-situ sensor comprising:
   an energy harvesting portion;
   a communication portion;
   a pressure sensor configured to provide, at a first time, a first measurement of interstitial pressure of surrounding tissue when located within tissue, and to provide, at a second time later than the first time, a second measurement of interstitial pressure of the surrounding tissue;
   a further sensor selected from a group comprising a pH sensor, a lactate sensor, an impedance sensor, a radiation sensor, a temperature sensor, or a sensor for bioelectrical potentials; and
   a controller coupled to the energy harvesting portion, the communication portion, the pressure sensor, and the further sensor,
   wherein said controller, said further sensor, said pressure sensor as well as the communication portion are configured to receive power from the energy harvesting portion,
   wherein the communication portion, under control of the controller, is configured to communicate information indicative of the first and second measurements provided by the pressure sensor and data indicative of the first and second measurements provided by said further sensor to an extracorporeal receiving entity,
   wherein the controller is configured to control said communication portion and/or said pressure sensor and/or said further sensor to consume less energy in case storage of energy by the energy harvesting portion drops below a threshold,
   wherein the pressure sensor comprises an amplifier and an Analog-to-Digital Converter (ADC), and
   wherein the controller is configured to control the ADC to narrow an amplitude region in which the ADC searches for the second measurement of the pressure sensor by using the first measurement of the pressure sensor to thereby reduce power consumption of the ADC.

2. The in-situ sensor according to claim 1, wherein the energy harvesting portion is configured to harvest energy provided by external electromagnetic and magnetic fields.

3. The in-situ sensor according to claim 1, wherein the communication portion is configured to evaluate sensor data received from the pressure sensor and/or said further sensor before communicating information indicative of the first and second measurements.

4. The in-situ sensor according to claim 1, wherein the communication portion is configured to send a unique identification.

5. The in-situ sensor according to claim 1, further comprising a storage portion configured to store the information indicative of the first and second measurements.

6. The in-situ sensor according to claim 1, wherein the communication portion is configured to communicate by inductive signal transfer or according to a Near Field Communication Standard.

7. The in-situ sensor according to claim 1, wherein the pressure sensor senses pressure based on piezo-effect or capacitance variation.

8. The in-situ sensor according to claim 1, wherein the in-situ sensor comprises a body comprising a biocompatible covering, and wherein said energy harvesting portion and said communication portion are arranged within the body.

9. The in-situ sensor according to claim 8, wherein the biocompatible covering comprises PTFE.

10. The in-situ sensor according to claim 1, wherein the body is formed for delivery into the tissue of the mammal by means of a biopsy needle having a size of Gauge G10 or smaller size.

11. The in-situ sensor according to claim 1, wherein the controller is configured to drive said amplifier at a lower current when storage of energy by the energy harvesting portion drops below the threshold.

12. The in-situ sensor according to claim 1, wherein the controller is configured to adjust said Analog-to-Digital Converter to a lower resolution when storage of energy by the energy harvesting portion drops below the threshold.

13. The in-situ sensor according to claim 1, wherein said Analog-to-Digital Converter is configured to generate compressed encoding of the information indicative of the first and second measurements.

14. The in-situ sensor according to claim 1, wherein said further sensor is a radiation damage sensor.

15. The in-situ sensor according to claim 1, wherein at least some of the portions of the in-situ sensor are implemented in adiabatic or quasi-adiabatic logic.

16. The in-situ sensor according to claim 1, wherein the tissue is malign or benign.

17. An in-situ sensor for being implanted within tissue of a mammal, the in-situ sensor comprising:
an energy harvesting portion;
a communication portion;
a pressure sensor configured to provide, at a first time, a first measurement of interstitial pressure of surrounding tissue when located within tissue, and to provide, at a second time later than the first time, a second measurement of interstitial pressure of the surrounding tissue;
a further sensor; and
a controller coupled to the energy harvesting portion, the communication portion, the pressure sensor, and the further sensor,
wherein said controller, said further sensor, said pressure sensor as well as the communication portion are configured to receive power from the energy harvesting portion,
wherein the communication portion, under control of the controller, is configured to communicate information indicative of the first and second measurements provided by the pressure sensor and data indicative of the first and second measurements provided by said further sensor to an extracorporeal receiving entity,
wherein the controller is configured to control said communication portion and/or said pressure sensor and/or said further sensor to consume less energy in case storage of energy by the energy harvesting portion drops below a threshold,
wherein the pressure sensor comprises an amplifier and an Analog-to-Digital Converter (ADC), and
wherein the controller is configured to control the ADC to narrow an amplitude region in which the ADC searches for the second measurement of the pressure sensor by using the first measurement of the pressure sensor to thereby reduce power consumption of the ADC.

\* \* \* \* \*